(12) United States Patent
Arnold et al.

(10) Patent No.: US 8,740,983 B1
(45) Date of Patent: Jun. 3, 2014

(54) SPINAL FUSION IMPLANTS AND RELATED METHODS

(75) Inventors: Benjamin Arnold, San Diego, CA (US); Erika Lin, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 12/945,787

(22) Filed: Nov. 12, 2010

Related U.S. Application Data

(60) Provisional application No. 61/260,396, filed on Nov. 11, 2009, provisional application No. 61/367,862, filed on Jul. 26, 2010.

(51) Int. Cl.
*A61F 2/44* (2006.01)

(52) U.S. Cl.
USPC ..................................... 623/17.16

(58) Field of Classification Search
USPC ........ 623/17.11–17.16; 606/247–249; 411/14
See application file for complete search history.

(56) References Cited

U.S. PATENT DOCUMENTS

| | | | |
|---|---|---|---|
| 4,463,753 A | 8/1984 | Gustilo | |
| 4,599,086 A | 7/1986 | Doty | |
| 4,743,256 A | 5/1988 | Brantigan | |
| 4,790,303 A | 12/1988 | Steffee | |
| 4,892,545 A | 1/1990 | Budde et al. | |
| 4,904,261 A | 2/1990 | Davis et al. | |
| 5,002,576 A | 3/1991 | Fritz et al. | |
| 5,062,850 A | 11/1991 | Haid, Jr. et al. | |
| 5,397,364 A | 3/1995 | Boyd et al. | |
| 5,405,391 A | 4/1995 | Hednerson et al. | |
| 5,534,031 A | 7/1996 | Matsuzaki et al. | |
| 5,549,612 A | 8/1996 | Worrick, III et al. | |
| 5,616,144 A | 4/1997 | Worrick, III et al. | |
| 5,713,899 A | 2/1998 | Godard et al. | |
| 5,843,082 A | 12/1998 | Benzel et al. | |
| 5,861,041 A | 1/1999 | Tienboon | |
| 5,876,456 A | 3/1999 | Bachmayer et al. | |
| 5,876,457 A | 3/1999 | Goldstein et al. | |
| 5,893,889 A | 4/1999 | Harrington | |
| 5,951,558 A | 9/1999 | Fiz | |
| 6,086,593 A * | 7/2000 | Bonutti | 606/87 |
| 6,099,531 A * | 8/2000 | Bonutti | 606/87 |
| 6,120,503 A | 9/2000 | Michelson | |
| 6,123,705 A | 9/2000 | Michelson | |
| 6,136,001 A | 10/2000 | Michelson | |
| 6,139,550 A | 10/2000 | Michelson | |
| 6,152,927 A | 11/2000 | Farris et al. | |
| 6,193,721 B1 | 2/2001 | Michelson | |
| 6,214,005 B1 | 4/2001 | Benzel et al. | |
| 6,235,059 B1 | 5/2001 | Benezech | |
| 6,258,089 B1 | 7/2001 | Campbell et al. | |
| 6,306,139 B1 | 10/2001 | Fuentes | |

(Continued)

FOREIGN PATENT DOCUMENTS

| | | |
|---|---|---|
| CA | 2444232 A1 | 8/1998 |
| CA | 2523814 A1 | 8/1998 |

(Continued)

*Primary Examiner* — Mary Hoffman
(74) *Attorney, Agent, or Firm* — Jonathan Sprangler; Heather Prado

(57) ABSTRACT

The present invention relates generally to medical devices and methods for use in spinal surgery. In particular, the disclosed system relates to an intervertebral spinal implant assembly sized and dimensioned for the lumbar spine implantable via an anterior or anterolateral approach. The device includes an implant, bone screws, and instruments for delivering the implant and bone screws.

18 Claims, 20 Drawing Sheets

(56) References Cited

U.S. PATENT DOCUMENTS

| | | |
|---|---|---|
| 6,306,170 B2 | 10/2001 | Ray |
| 6,364,880 B1 | 4/2002 | Michelson |
| 6,371,986 B1 | 4/2002 | Bagby |
| 6,395,030 B1 | 5/2002 | Songer et al. |
| 6,423,063 B1 | 7/2002 | Bonutti |
| 6,468,311 B2 | 10/2002 | Boyd et al. |
| 6,471,724 B2 | 10/2002 | Zdeblick et al. |
| 6,485,517 B1 | 11/2002 | Michelson |
| 6,540,785 B1 | 4/2003 | Gill et al. |
| 6,558,423 B1 | 5/2003 | Michelson |
| 6,558,424 B2 | 5/2003 | Thalgott |
| 6,562,073 B2 | 5/2003 | Foley |
| 6,576,017 B2 | 6/2003 | Foley et al. |
| 6,579,290 B1 * | 6/2003 | Hardcastle et al. ........... 606/247 |
| 6,626,907 B2 | 9/2003 | Campbell et al. |
| 6,652,525 B1 | 11/2003 | Assaker et al. |
| 6,669,700 B1 | 12/2003 | Farris et al. |
| 6,682,561 B2 | 1/2004 | Songer et al. |
| 6,730,127 B2 | 5/2004 | Michelson |
| 6,911,045 B2 | 6/2005 | Shimp |
| 6,916,320 B2 | 7/2005 | Michelson |
| 6,926,718 B1 | 8/2005 | Michelson |
| 6,969,390 B2 | 11/2005 | Michelson |
| 6,972,019 B2 | 12/2005 | Michelson |
| 7,001,385 B2 * | 2/2006 | Bonutti ........................... 606/60 |
| 7,001,387 B2 | 2/2006 | Farris et al. |
| 7,033,394 B2 | 4/2006 | Michelson |
| 7,041,135 B2 | 5/2006 | Michelson |
| 7,063,701 B2 | 6/2006 | Michelson |
| 7,077,844 B2 | 7/2006 | Michelson |
| 7,094,239 B1 | 8/2006 | Michelson |
| 7,112,222 B2 | 9/2006 | Fraser et al. |
| 7,137,984 B2 | 11/2006 | Michelson |
| 7,163,561 B2 | 1/2007 | Michelson |
| 7,172,627 B2 | 2/2007 | Fiere et al. |
| 7,226,482 B2 | 6/2007 | Messerli et al. |
| 7,232,464 B2 | 6/2007 | Mathieu et al. |
| 7,235,105 B2 | 6/2007 | Jackson |
| 7,255,698 B2 | 8/2007 | Michelson |
| 7,267,690 B2 | 9/2007 | Felt |
| 7,323,011 B2 | 1/2008 | Shepard et al. |
| 7,491,237 B2 | 2/2009 | Randall et al. |
| 7,621,956 B2 | 11/2009 | Paul et al. |
| 7,621,960 B2 | 11/2009 | Boyd et al. |
| 7,637,951 B2 | 12/2009 | Michelson |
| 7,637,954 B2 | 12/2009 | Michelson |
| 7,651,497 B2 | 1/2010 | Michelson |
| 7,662,185 B2 | 2/2010 | Alfaro et al. |
| 7,776,093 B2 | 8/2010 | Wolek et al. |
| D623,750 S | 9/2010 | Duffield et al. |
| 7,846,207 B2 | 12/2010 | Lechmann et al. |
| 7,914,554 B2 | 3/2011 | Michelson |
| 7,918,891 B1 * | 4/2011 | Curran et al. .............. 623/17.16 |
| 8,048,075 B2 | 11/2011 | Michelson |
| 8,137,405 B2 * | 3/2012 | Kostuik et al. ............. 623/17.16 |
| 2005/0101960 A1 * | 5/2005 | Fiere et al. ....................... 606/72 |
| 2005/0177245 A1 | 8/2005 | Leatherbury et al. |
| 2005/0187552 A1 | 8/2005 | Michelson |
| 2006/0079961 A1 | 4/2006 | Michelson |
| 2006/0085071 A1 | 4/2006 | Lechman et al. |
| 2006/0122703 A1 | 6/2006 | Aebi et al. |
| 2006/0200166 A1 | 9/2006 | Hanson et al. |
| 2006/0206208 A1 | 9/2006 | Michelson |
| 2006/0229620 A1 * | 10/2006 | Rothman et al. ................. 606/69 |
| 2006/0282165 A1 | 12/2006 | Pisharodi |
| 2007/0233253 A1 | 10/2007 | Bray et al. |
| 2007/0270965 A1 | 11/2007 | Ferguson |
| 2008/0082173 A1 | 4/2008 | Delurio et al. |
| 2008/0177307 A1 | 7/2008 | Moskowitz et al. |
| 2008/0249569 A1 | 10/2008 | Waugh et al. |
| 2008/0249575 A1 * | 10/2008 | Waugh et al. ................. 606/305 |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2009/0088849 A1 | 4/2009 | Armstrong et al. |
| 2009/0099659 A1 | 4/2009 | Oh et al. |
| 2009/0105831 A1 | 4/2009 | Jones et al. |
| 2009/0157186 A1 | 6/2009 | Magerl |
| 2009/0182430 A1 | 7/2009 | Tyber et al. |
| 2009/0192613 A1 * | 7/2009 | Wing et al. .................. 623/17.11 |
| 2009/0192615 A1 * | 7/2009 | Tyber et al. ................. 623/17.16 |
| 2009/0210062 A1 | 8/2009 | Thalgott et al. |
| 2009/0210063 A1 | 8/2009 | Barrett |
| 2009/0224023 A1 | 9/2009 | Moskowitz et al. |
| 2009/0234455 A1 | 9/2009 | Moskowitz et al. |
| 2009/0259256 A1 | 10/2009 | Miller |
| 2009/0270991 A1 | 10/2009 | Michelson |
| 2010/0049324 A1 | 2/2010 | Valdevit et al. |
| 2010/0057206 A1 | 3/2010 | Duffield et al. |
| 2010/0087925 A1 * | 4/2010 | Kostuik et al. ............. 623/17.16 |
| 2010/0106249 A1 * | 4/2010 | Tyber et al. ................. 623/17.11 |
| 2010/0125334 A1 | 5/2010 | Krueger |
| 2010/0145460 A1 * | 6/2010 | McDonough et al. ...... 623/17.16 |
| 2010/0185288 A1 | 7/2010 | Carls et al. |
| 2010/0204739 A1 | 8/2010 | Bae et al. |
| 2010/0217393 A1 * | 8/2010 | Theofilos ................... 623/17.11 |
| 2010/0249935 A1 | 9/2010 | Slivka et al. |
| 2011/0313528 A1 * | 12/2011 | Laubert et al. ............. 623/17.16 |

FOREIGN PATENT DOCUMENTS

| | | |
|---|---|---|
| CA | 2533713 A1 | 8/1998 |
| DE | 29511146 U1 | 1/1996 |
| DE | 19630256 A1 | 1/1998 |
| EP | 0179695 A1 | 4/1986 |
| EP | 0560140 A1 | 9/1993 |
| FR | 2727003 A1 | 5/1996 |
| FR | 2727619 A1 | 6/1996 |
| FR | 2923155 A1 | 5/2009 |
| JP | 4114644 A | 4/1992 |
| SU | 1519677 A1 | 11/1989 |
| SU | 1715338 A1 | 2/1992 |
| WO | WO-9525474 A1 | 9/1995 |
| WO | WO-9720526 A1 | 6/1997 |
| WO | WO-9723175 A1 | 7/1997 |
| WO | WO-9963913 A2 | 12/1999 |
| WO | WO-9963914 A1 | 12/1999 |
| WO | WO-02065957 A2 | 8/2002 |
| WO | WO-2007098288 A2 | 8/2007 |
| WO | WO-2009064644 A1 | 5/2009 |
| WO | WO-2009071153 A1 | 6/2009 |
| WO | WO-2009091775 A2 | 7/2009 |
| WO | WO-2009092961 A2 | 7/2009 |
| WO | WO-2009099559 A2 | 8/2009 |
| WO | WO-2009144671 A1 | 12/2009 |
| WO | WO-2010028045 A1 | 3/2010 |
| WO | WO-2010028095 A1 | 3/2010 |
| WO | WO-2010079993 A2 | 7/2010 |

* cited by examiner

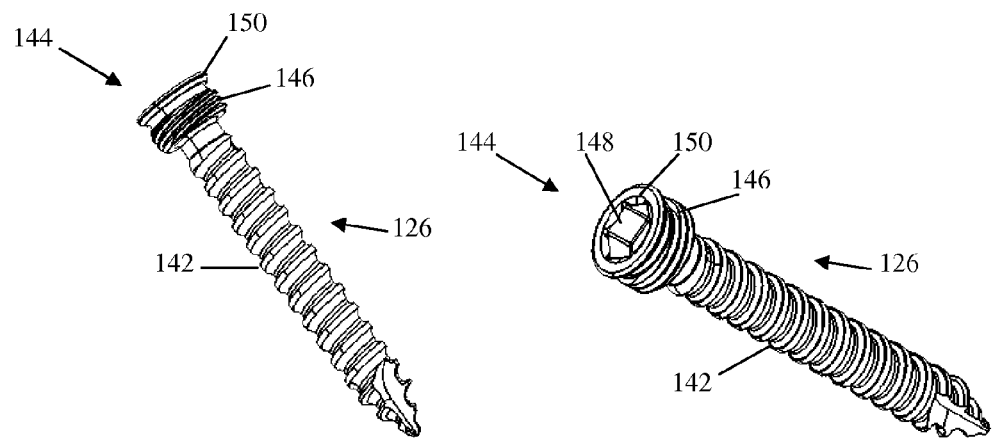
*FIG. 5*          *FIG. 6*
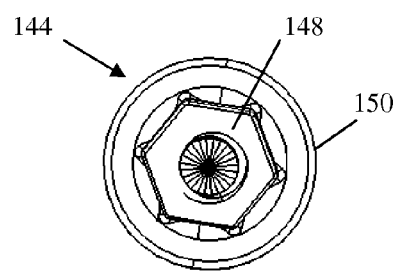
*FIG. 7*
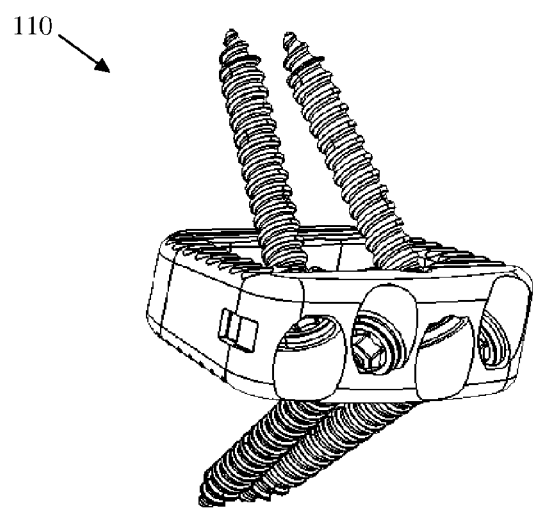
*FIG. 8*

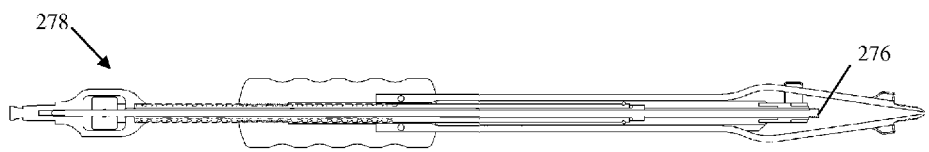
*FIG. 29*
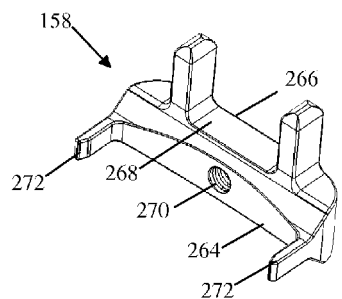 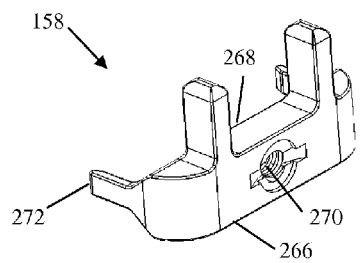
*FIG. 30* *FIG. 31*

SPINAL FUSION IMPLANTS AND RELATED METHODS

CROSS REFERENCE TO RELATED APPLICATIONS

This application is a non-provisional patent application claiming the benefit of priority from U.S. Provisional Patent Application Ser. No. 61/260,396, filed on Nov. 11, 2009, and U.S. Provisional Patent Application Ser. No. 61/367,862, filed on Jul. 26, 2010, the entire contents of which are hereby expressly incorporated by reference into this disclosure as if set forth in its entirety herein.

FIELD

The present invention relates generally to spinal surgery and, more particularly, to a device for spinal fusion comprising a spinal fusion implant of non-bone construction to be introduced into any variety of spinal target sites.

BACKGROUND

Currently there are nearly 500,000 spine lumbar and cervical fusion procedures are performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF) procedures provide unparalleled access to a desired spinal target site. The ALIF technique involves approaching the spine through the abdomen and exposing the front of the spine, as opposed to the side or the back. Approaching the spine this way generally allows for greater exposure and a more complete excision of the damaged disc. Introducing the intervertebral implant serves to restore the height between adjacent vertebrae ("disc height"), which reduces if not eliminates neural impingement commonly associated with a damaged or diseased disc.

SUMMARY

In a preferred aspect, the spinal fusion implant includes a body configured for implantation between a superior and inferior vertebra, having a top surface and a bottom surface, an anterior height and a posterior height, and a fusion aperture defined by an anterior wall, a posterior wall, and first and second lateral walls. In some implementations, the anterior height of the body is greater than the posterior height of the body, such that the top surface creates a posterior-to-anterior angle relative to the horizontal axis. The posterior-to-anterior angle may be between 5° and 15°.

The body may be constructed of radiolucent, non-bone material. At least one of the top surface and bottom surface may include anti-migration features. The body may also include at least one radiopaque marker. In some implementations, the body may include an engagement groove in the lateral walls dimensioned to receive a gripping element of an inserter.

The spinal fusion implant also includes a plurality of fastener apertures extending through the anterior wall at oblique angles relative to a horizontal axis. Each of the fastener apertures is dimensioned to receive a bone fastener for insertion into one of the superior or inferior vertebrae. The bone fasteners have a head, a shank and a collar disposed between the head and shank. The collar of the bone fastener may be at least partially threaded.

The fastener apertures have an anterior diameter that is greater than the posterior diameter. The fastener apertures further include an annular groove dimensioned to retain the head of the bone fastener therein. In some implementations, the fastener apertures may further comprise a visualization marker proximal to the annular groove. The fastener apertures may also include a ledge, wherein the ledge has a diameter that is smaller than the head of the bone fastener, such that the ledge is temporarily deformed while the head of the bone fastener is passing said ledge during insertion.

Implementations may include one or more of the following features. For example, fastener apertures extending through the anterior wall of the implant body may at angles between 35° and 55° relative to the horizontal axis. Preferably, the fastener apertures extend through the anterior wall of the body at a 45° angle relative to the horizontal axis.

The fastener apertures may also extend through the anterior wall at angles oblique to the longitudinal axis. In some implementations, the angles oblique to the longitudinal axis may be convergent. Preferably, the angles are between 5° and 15° relative to the longitudinal axis. More preferably, the fastener apertures extend through the anterior wall at a 12° angle relative to the longitudinal axis.

In a preferred embodiment, the spinal fusion implant includes four fastener apertures. Two of the apertures may be dimensioned to receive bone fasteners for insertion into the inferior vertebra, and two of the apertures may be dimensioned to receive bone fasteners for insertion into the superior vertebra.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 5 is a perspective view of a bone screw, according to one example embodiment, for use with the spinal implant of FIG. 1;

FIG. 6 is a second perspective view of the bone screw of FIG. 5;

FIG. 7 is a top view of the bone screw of FIG. 5;

FIG. 8 is a perspective view of the spinal implant assembly including the spinal implant of FIG. 1 and four of the bone screws of FIG. 5;

FIG. 29 is a partial cross-section of the insertion instrument of FIG. 28;

FIG. 30 is a perspective view of one embodiment of an inserter adapter for use with the insertion instrument of FIG. 28;

FIG. 31 is an alternate perspective view of the inserter adapter of FIG. 30;

DESCRIPTION OF THE PREFERRED EMBODIMENT

Figure 1:
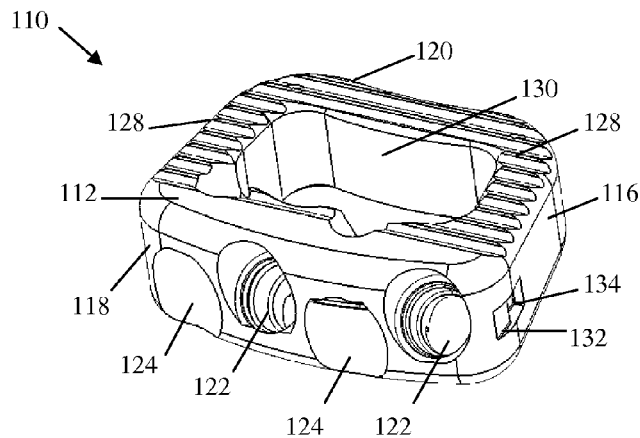
FIG. 1 is a perspective view of a spinal implant, according to one example embodiment.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

FIGS. 1-11 illustrate a spinal fusion implant 110 according to a first broad aspect of the present invention. The spinal fusion implant 110 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 110 includes a top surface 112, a bottom surface 114, two lateral sides 116, an anterior side 118, and a posterior side 120 (each defined relative to the regions of the target disc space when implanted). According to a preferred method of implantation the spinal fusion implant 110 may be implanted from an anterior approach such that anterior side 118 is the trailing side and posterior side 120 is the leading side during insertion. The anterior side 118 includes a pair of upper screw holes 122 and a pair of lower screw holes 124, each for receiving a bone screw 126 therethrough. The screw holes are positioned such that there is a lateral upper screw hole 122, a medial upper screw hole 122, a lateral lower screw hole 124, and a medial lower screw hole 124.

According to a preferred embodiment, the spinal fusion implant 110 includes at least one radiopaque marker 129. In one embodiment, the implant 110 includes one or more pin elements 129 disposed within the posterior side 120 of the implant 110. The pin element 129 may be manufactured from any of a variety of suitable radiopaque materials, including but not limited to a metal. The one or more pin elements 129 may each comprise a unitary element extending through the top surface 112 and bottom surface 114. Alternatively, each pin element 129 may comprise a shorter element which only extends through a single surface. Alternatively, each pin element 129 may comprise a shorter element that does not extend beyond either surface.

The spinal fusion implant 110 of the present invention may be used to provide temporary or permanent fixation along an orthopedic target site. Once deposited in the intervertebral disc space, the spinal implant 110 effects spinal fusion over time as the natural healing process integrates and binds the implant 110 within the intervertebral space by allowing a bony bridge to form through the implant 110 and between the adjacent vertebral bodies. Top surface 112 and opposed bottom surface 114 are both adapted for contact with the upper and lower vertebra adjacent the disc space. Bone screws 126 may be introduced through the screw holes 122, 124 and into the adjacent vertebral bodies to fix the implant 10 in the desired position within the disc space.

The top and bottom surfaces 112, 114 preferably include anti-migration features situated along at least a portion of their area. Anti-migration features are designed to increase the friction between the spinal fusion implant 110 and the adjacent contacting surfaces of the vertebral bodies so as to further prohibit migration of the spinal fusion implant 110 after placement and during the propagation of natural bony fusion. Such anti-migration features may include ridges (or teeth) 128 provided along at least a portion of the top surface 112 and/or bottom surface 114.

Figure 3:
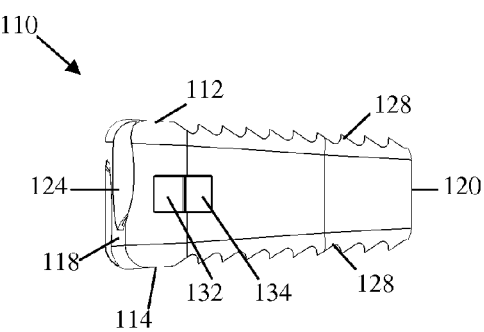
FIG. 3 is a side view of the spinal implant of FIG. 1.

According to an additional embodiment (as depicted in FIG. 3), the top and bottom surfaces 112, 114 may be angled between the anterior side 118 and posterior side 120. In lumbar and cervical applications, the posterior side 10 will preferably be shorter in height than the anterior side 118 such that the implant 10 tapers down from anterior side 118 to posterior side 120. For example, the posterior-to-anterior angle of the tapered top and bottom surfaces 112, 114 may range from 5° and 15° relative to a horizontal axis, and preferably 8° to 12°. In this manner, the implant 110 helps maintain the adjacent vertebral bodies in lordosis, which is the natural curvature found in the lumbar and cervical regions of the spine. The top and bottom surfaces 112, 114 may be configured in any number of suitable shapes to better match the natural contours of the vertebral end plates, such as, for example, concave, convex, or a combination of concave and convex.

Figure 2:
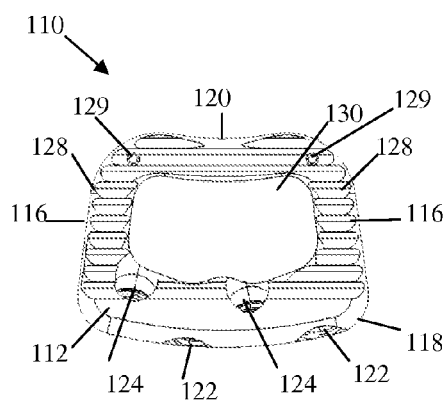
FIG. 2 is a top view of the spinal implant of FIG. 1.

As best viewed in FIG. 2, the implant 10 includes a central cavity 130 extending through the top and bottom surfaces 112, 114. The generally D-shaped area of the cavity 130 is provided to maximize the size of the cavity 130 to allow the greatest area for bony through-growth, however cavity 130 may be provided in any number of other suitable shapes, including but not limited to generally circular, oblong, and rectangular. Additionally, multiple cavities may be provided and separated by one or more support walls.

Fusion may be facilitated or augmented by introducing or positioning various osteoinductive materials within cavity 130 and/or adjacent to the spinal fusion implant 110. Such osteoinductive materials may be introduced before, during, or after insertion of the exemplary spinal fusion implant 110, and may include (but are not necessarily limited to) autologous bone harvested from the patient receiving the spinal fusion implant 110, bone allograft, bone xenograft, any number of non-bone implants (e.g. ceramic, metallic, polymer), bone morphogenic protein, and bio-resorbable compositions, including but not limited to, any of a variety of poly (D, L-lactice-co-glycolide) based polymers.

FIG. 3 illustrates a lateral side 116 according to one example embodiment. Lateral sides 116 each include an engagement groove 132 opening in anterior side 118 and extending distally to a point short of posterior side 120. At the distal-most portion of the engagement grooves 132, the groove extends deeper into the lateral side wall 116 forming a gripping indent 134. As described below, engagement grooves 132 are configured to mate with an array of insertion instruments.

Figure 4:
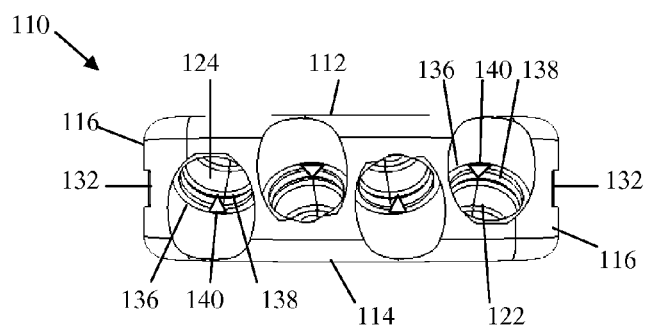
FIG. 4 is a front view of the spinal implant of FIG. 1.
Figure 9:
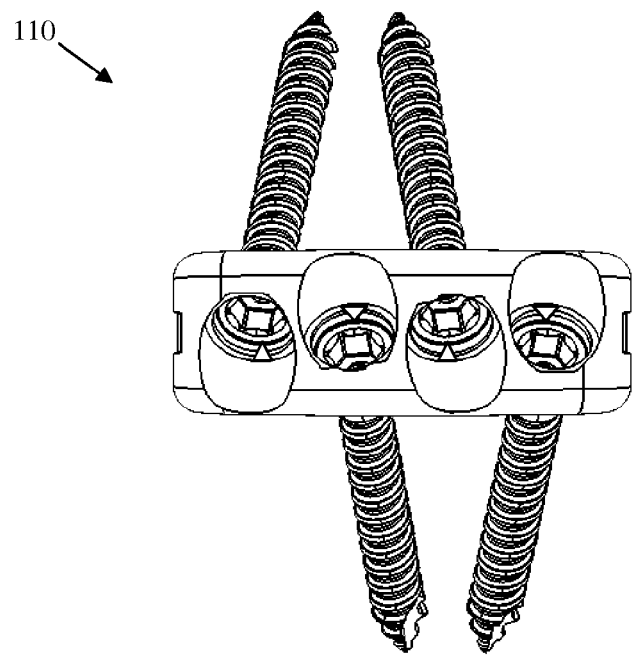
FIG. 9 is a front view of the spinal implant assembly of FIG. 8.
Figure 10:
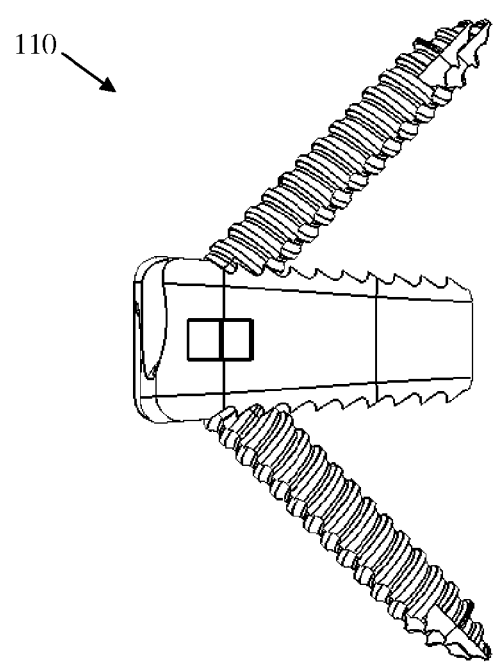
FIG. 10 is a side view of the spinal implant assembly of FIG. 8.
Figure 11:
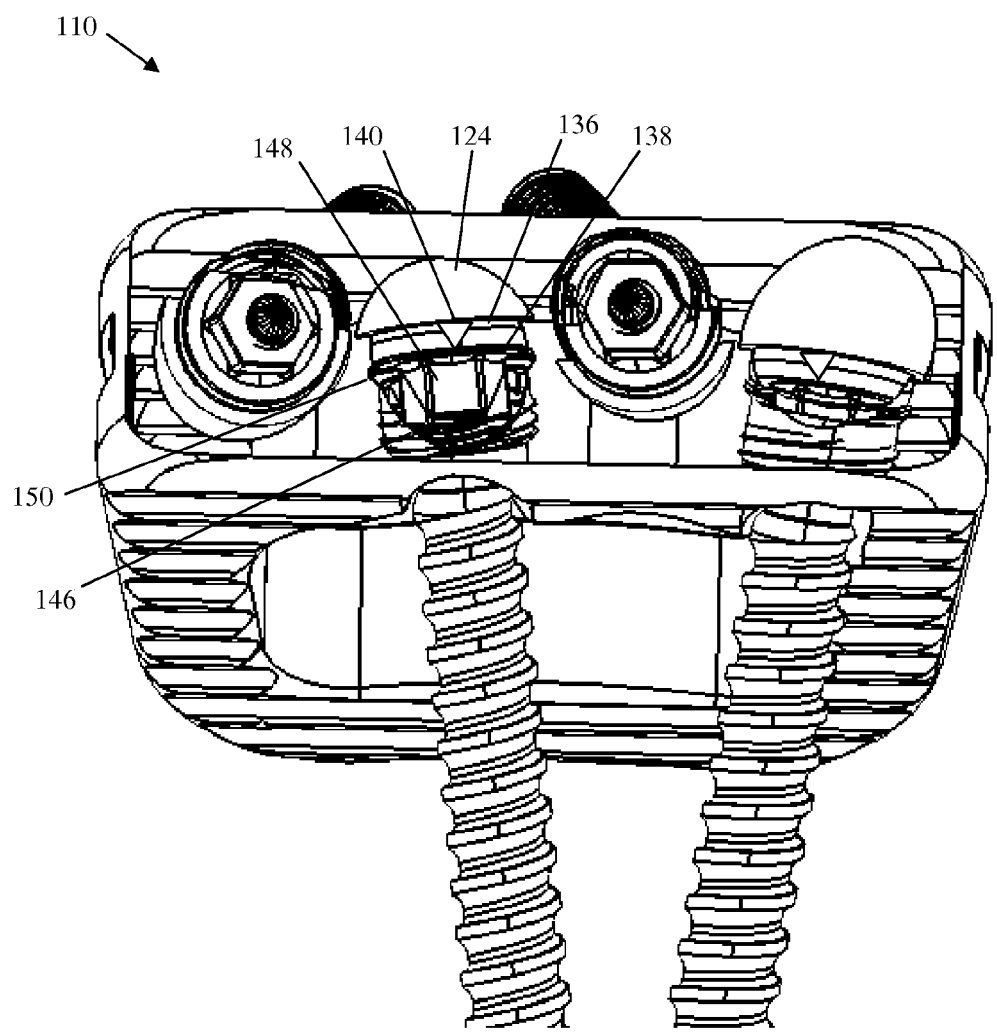
FIG. 11 is a partial-cross section view of the spinal implant of FIG. 8 showing the interaction between the spinal implant of FIG. 1 and the bone screw of FIG. 5.

As best appreciated in FIGS. 1 and 4, the upper screw holes 122 pass through the anterior side 118 at an angle such that when the bone screws 126 are inserted into the upper screw holes 122, they extend from the implant 110 at an angle and penetrate into the vertebral body inferior to the implant 110. By way of example only, the upper screw holes 122 may be angled such that the bone screws 126 penetrate into the vertebral body at an angle between 35 and 55 degrees, and preferably 45 degrees. Lower screw holes 124 also pass through the anterior side 118 at an angle, but in the opposite direction of the upper screw holes 122. Thus, when the bone screw 126 is inserted into the lower screw holes 124, it extends from the implant 110 at an angle and penetrates the vertebral body superior to the implant 110. By way of example, the lower screw holes 124 may be angled such that the lower bone screws 126 penetrate into the vertebral body at an angle between 35 and 55 degrees, and preferably 45 degrees. The lateral screw holes 122, 124 may also be angled such that the distal end of the bone screws 126 converge towards each other. By way of example, the screw holes may be oriented such that the bone screws are angled medially between 5 and 15 degrees, and preferably 12 degrees. The medial bone screw holes 122, 124 may also be angled such that the distal end of the bone screws 126 converge towards each other. By way of example, the bone screw holes may be oriented such that the bone screws are angled medially between 5 and 15 degrees, and preferably 10 degrees.

With reference to FIG. 4, screw holes 122 and 124 are equipped with a ledge 136. The ledge 136 acts as a stop for instruments including, but not limited to, the instruments described in FIGS. 32-34 and 41-42. Particularly, the ledge 136 may act as a stop for the retractable awl cover 298 and driver cover 314. The covers 298, 314 initially fit within the screw holes 122, 124 but are restricted from further penetration at the ledge 136. The retractable awl 280 and the guided straight driver 312 continue to travel and emerge from the cover 298 or 314 within the bone screw holes 122, 124.

Past (distal to) the ledge 136, the screw hole 122 or 124 tapers inward until the diameter is less than diameter of the bone screw rim 150. The screw head 144 deforms the implant enough to travel past the point at which its diameter is larger than the hole to an annular groove 138 formed about an anterior surface within the screw hole 122 or 124. The annular groove 138 cooperates with the screw 126 when fully inserted into the screw hole 122, 124 to prevent the bone screw 126 from backing out of the screw hole 122, 124. Once the rim 150 enters the groove 138, it is prevented from moving back out of the annular groove 138. Beyond (distal to) the annular groove 138, the hole 122 or 124 continues to taper inward. The degree of taper is such that the threaded neck 146 of the bone screw 126 will bite into the inner wall of the implant once the screw 126 advances enough for the rim 10 to enter the annular groove 138. This provides tactile feedback to the user that the bone screw 126 is fully seated.

As illustrated in FIG. 4, the screw holes 122, 124 may also be provided with one or more visualization markers (e.g. arrows 140) in between the ledge 136 and the annular groove 138. Arrows 140 provide a visual indication that the screw 126 has been properly positioned beyond the annular groove 138. For example, the entire arrow is not visible (i.e. it is blocked from view of the user by the screw head 144 until the screw 126 is fully seated within the annular groove 138).

With reference to FIGS. 5-7, there is shown a bone screw 126 for use with the spinal fusion implant 110. The bone screw 126 has a threaded shaft 142, a head 144, and a threaded neck 146 separating the threaded shaft 142 and the head 144. The head 144 further comprises a tooling recess 148, for example a hex recess, for engaging a driver (for example, driver 312 shown in FIG. 41) and a rim 150. The diameter of the rim 150 is slightly larger than the diameter of the interior of the screw hole 122 or 124 adjacent to the annular groove 138. As the bone screw 126 is driven into the vertebra through screw hole 122 or 124, the rim 150 slightly deforms the area above the annular groove 138 thereby allowing the bone screw 126 to pass into the annular groove 138. The area above the annular groove 138 reforms, capturing the head 144 thereby preventing unwanted backout of the bone screw 126. By way of example only, the diameter of the screw head 144 may be 6.985 mm while the diameter of the screw hole 122 or 124 may be 6.731 mm. As pictured in FIG. 11, when the bone screw 126 is fully seated, the visualization arrow 140 below the ledge 136 within the screw hole 122 or 124 will be fully visible. This indicates to the user that the bone screw 126 is fully captured in the annular groove 38. FIGS. 8-11 show perspective, anterior, lateral, and cross-sectional views of the spinal fusion implant 110 with the screws 126 fully positioned.

Figure 12:
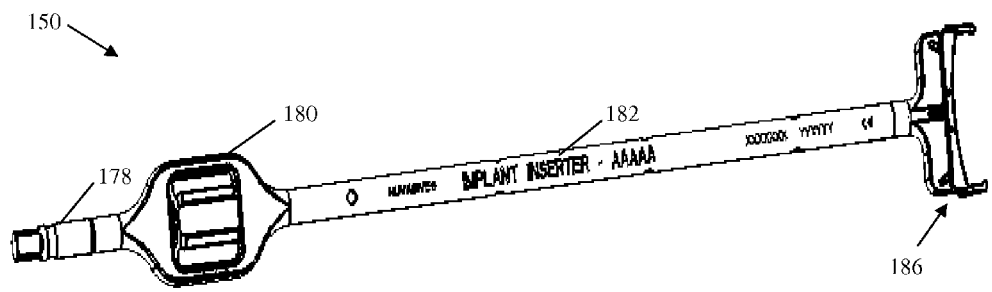
FIG. 12 is an insertion instrument according to a first embodiment.
Figure 13:
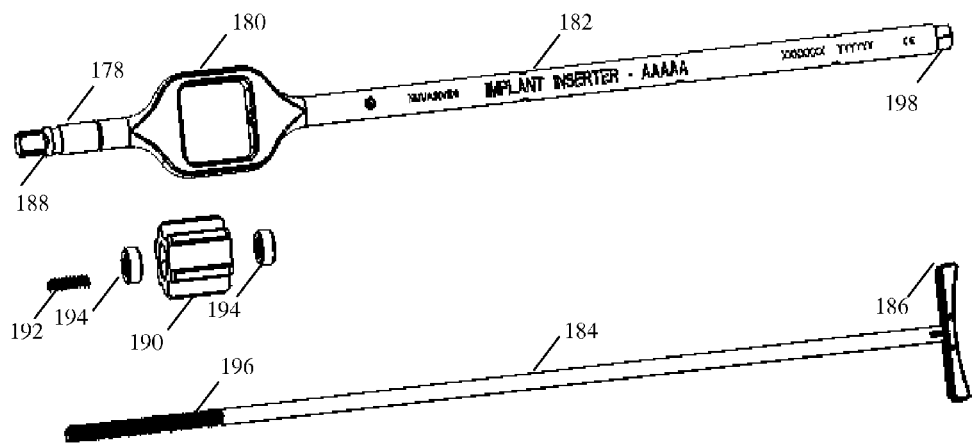
FIG. 13 is an exploded view of the insertion instrument of FIG. 12.

As described in FIGS. 12-31, the present invention includes a plurality of inserters which provide the user with a suite of choices for implanting the implant 110. According to a broad aspect of the present invention, the insertion instruments include a handle 178, a thumbwheel housing 180, an elongate tubular element 182, an inserter shaft 184, and a distal inserter head 186, as illustrated in FIGS. 12-13.

The handle 178 is generally disposed at the proximal end of the insertion instrument 152. The handle 178 may be further equipped with a universal connector 188 to allow the attachment of accessories for ease of handling of the insertion instrument 152 (e.g. a straight handle, or a T-handle, not shown). The handle 178 is fixed to the thumbwheel housing 180 allowing easy handling by the user. By way of example, the thumbwheel housing 180 holds a thumbwheel 190, a set screw 192, and at least one spacer 194. Because the handle 178 is fixed, the user has easy access to the thumbwheel 190 and can stably turn the thumbwheel 190 relative to the thumbwheel housing 180. Additionally, the relative orientation of the thumbwheel housing 180 to the handle 178 orients the user with respect to the distal insertion head 186. The inserter shaft 184 is attached to the thumbwheel 190 and is freely rotatable with low friction due to the spacer 194. The user may then employ the thumbwheel 190 to rotate the inserter shaft 184 thereby advancing it towards distal inserter head 186.

The elongate tubular element 182 is generally cylindrical and of a length sufficient to allow the device to span from the surgical target site to a location sufficiently outside the patient's body so the handle 178 and thumbwheel housing 180 can be easily accessed by a clinician or a complimentary controlling device. The elongate tubular element 182 is dimensioned to receive a spring 196 and the proximal end of the inserter shaft 184 into the inner bore 198 of the elongate tubular element 182.

FIGS. 12-17 detail an insertion instrument 152 according to a first embodiment of the present invention, preferably adapted for insertion from an anterior approach. The distal inserter head 186 is comprised of a fixed inserter base 202 extending generally perpendicularly from elongate tubular element 182, an actuating member 204 extending generally perpendicularly from the inserter shaft 184 and two gripping arms 206.

Figure 14:
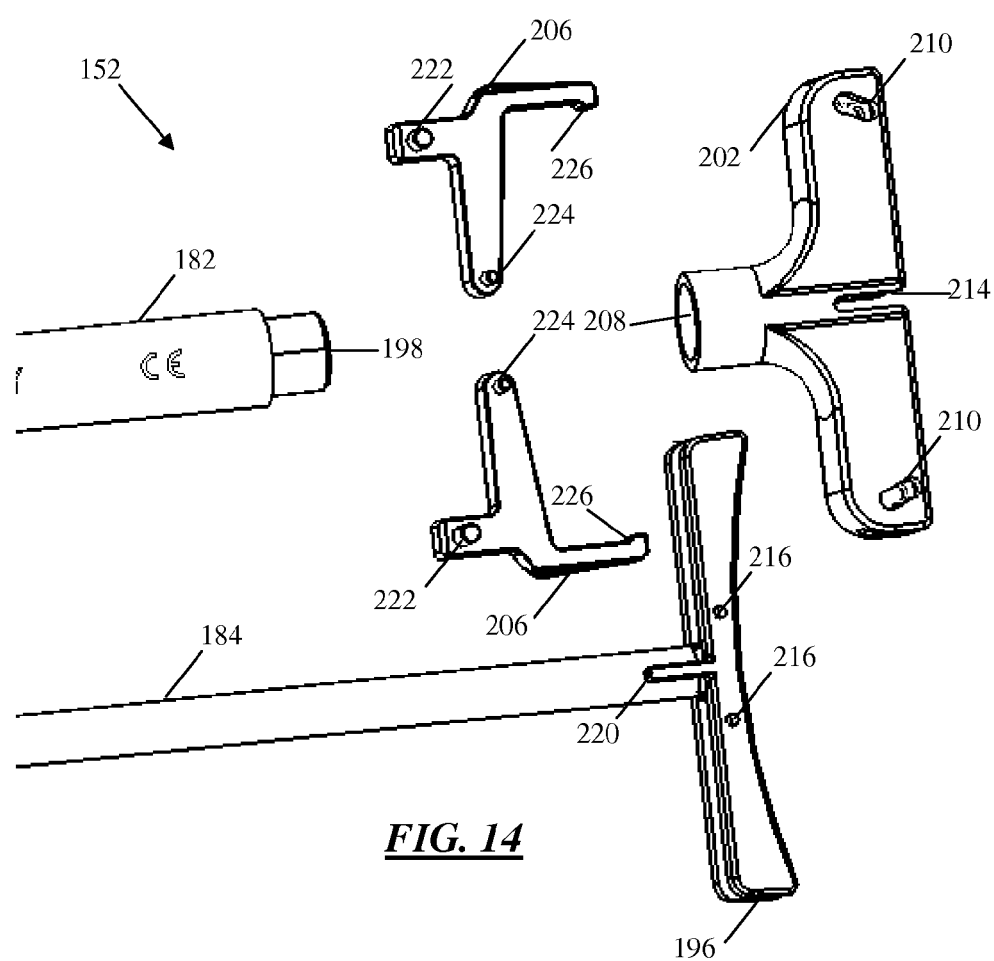
FIG. 14 is an exploded view of the insertion head of the insertion instrument of FIG. 12.
Figure 15:
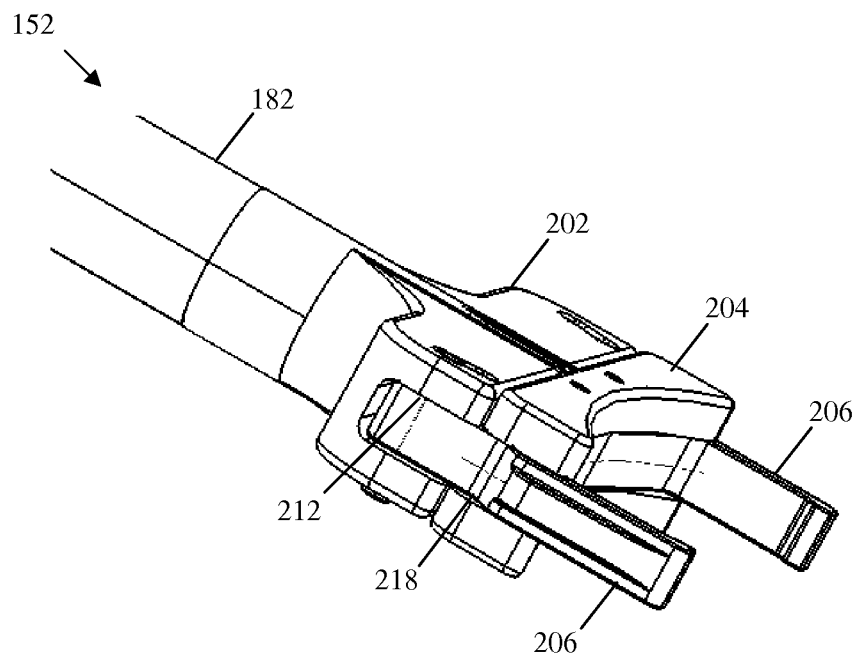
FIG. 15 is a perspective, detailed view of the lateral channels of the gripping instrument of FIG. 12.

As best viewed in FIGS. 14-15, the inserter base 202 contains a central aperture 208, two guide slots 210, and two lateral channels 212, and a central slot 214. The central aperture 208 on the inserter base 202 is sized and dimensioned to allow slidable passage over the inserter shaft 184.

Actuating member 204 contains two pin-receiving apertures 216, two lateral channels 218, and a central protrusion 220. The pin-receiving apertures 216 are capable of receiving the pivot pins 224 centrally located on the gripping arms 206. This provides a fixed point for the gripping arm to rotate in relation to the actuating member 204. Each lateral channel 218 is sized and dimensioned such that the lateral aspect of each gripping arm 206 is seated within the lateral channel 218. The central protrusion 220 is sized and dimensioned to be slideably received by central slot 214 on the inserter base 202. As the central protrusion 220 of the actuating member 204 is being advanced by the inserter shaft 184, it travels along the appropriate path within the central slot 214.

The two gripping arms 206 each contain a laterally-disposed guide post 222, a medially-disposed pivot pin 224, and a terminal engagement hook 226. Gripping arms 206 are seated within the inserter base 202 via the lateral channels 212 and seated within the actuating member 204 via the lateral channels 218. Gripping arms 206 are attached to the actuating member 204 via the pivot pins 224 received within the pin-receiving apertures 216 on the actuating member 204. The gripping arms 206 are pivotably disposed within the fixed inserter base 202 via the guide posts 222 positioned within the guide slots 210.

Figure 16:
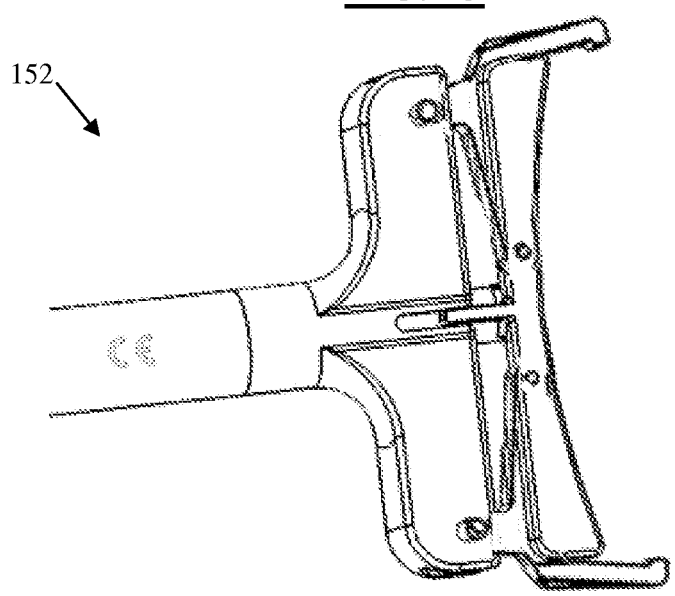
FIG. 16 is a perspective view of the insertion instrument of FIG. 12 with the gripping arms in an open position.
Figure 17:
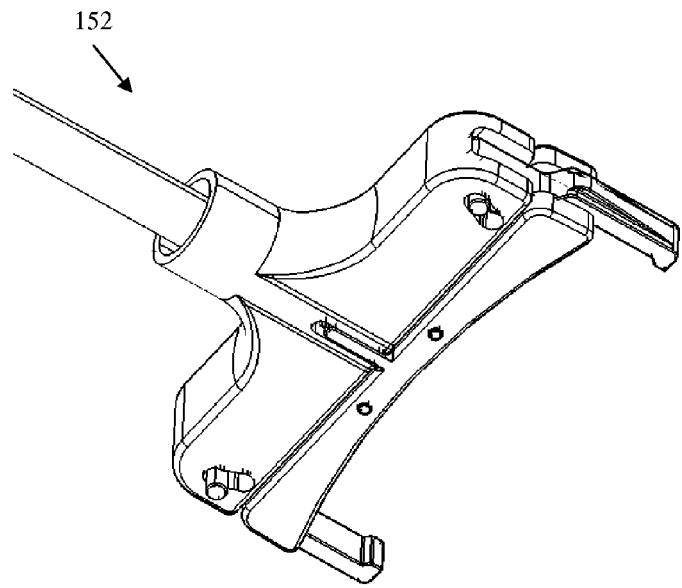
FIG. 17 is a perspective view of the insertion instrument of FIG. 12 with the gripping arms in an open position.
Figure 18:
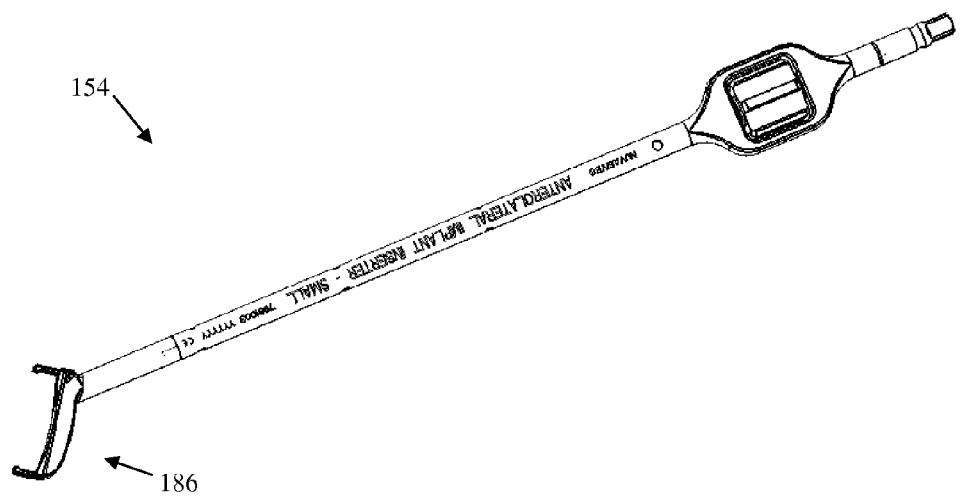
FIG. 18 is an insertion instrument according to a second embodiment.

As illustrated in FIG. 16, the initial position of the inserter shaft 184 is a fully advanced such that the actuating member 204 is at a distance distal to the inserter base 202 and the guide posts 222 are placed in a first, distal position within the guide slots 210. The gripping arms 206 may be then be placed adjacent to the engagement grooves 132 of the spinal fusion implant 110. The rotation of the thumbwheel 190 in the clockwise direction causes the inserter shaft 184 to retreat within the elongate tube member 182, which will result in pulling the actuating member 204 closer towards the inserter base 202. This movement will cause the gripping arms 206 to pivot about the pivot pins 224 of the gripping arms 206. The gripping arms 206 are guided medially and proximally via the guide slots 210 on the inserter base 202 towards the second, proximal position. (FIG. 17) When the inserter shaft 184 is fully retracted within the elongate tubular member 182 and the actuating member 204 has reached a final position with the inserter base 202, the gripping hooks 226 are releaseably engaged to the engagement grooves 132 of the spinal fusion implant 110 such that the insertion instrument 152 is stabilized relative to the spinal fusion implant 110. Once the implant 110 has been successfully inserted into the disc space, the thumbwheel 190 direction is reversed, thereby de-coupling the inserter 152 from the implant 110.

FIGS. 18-22 detail an insertion instrument 154 according to a second embodiment of the present invention, preferably adapted for insertion from an antero-lateral approach. The distal insertion head 186 includes a fixed inserter body 228 and a moveable gripping arm 230.

Figure 19:
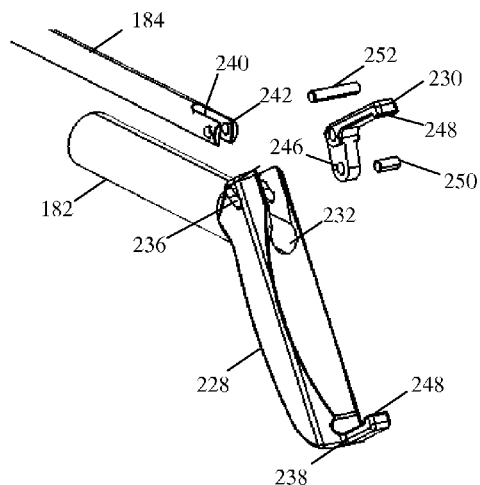
FIG. 19 is an exploded view of the insertion head of the insertion instrument of FIG. 18.
Figure 20:
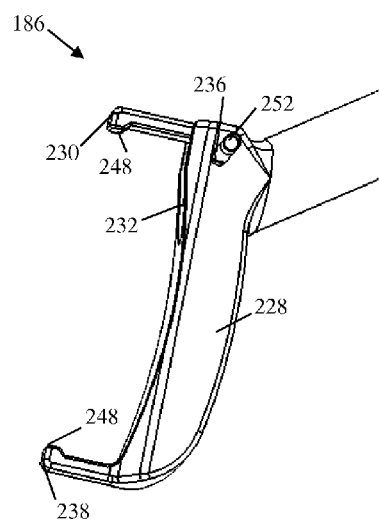
FIG. 20 is a side view of the insertion instrument of FIG. 18.
Figure 21:
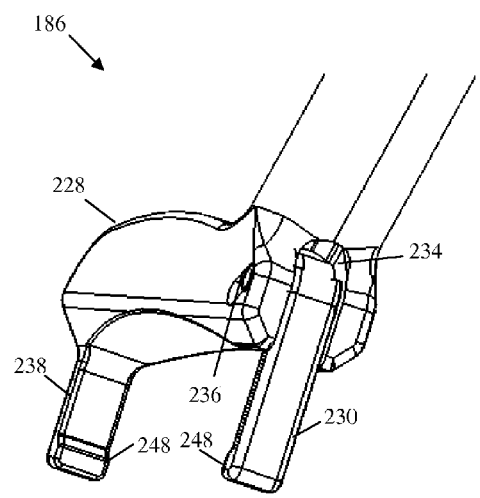
FIG. 21 is a detailed, perspective view of the lateral channel of the gripping arm of FIG. 18.
Figure 22:
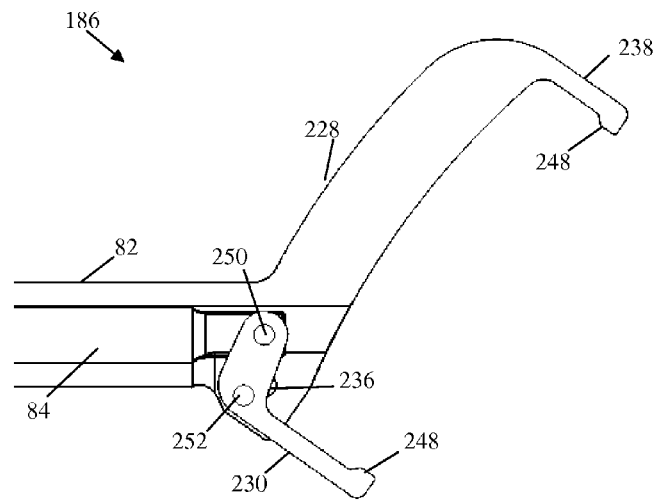
FIG. 22 is a cross-sectional side view showing the insertion mechanism of the insertion instrument of FIG. 18.
Figure 23:
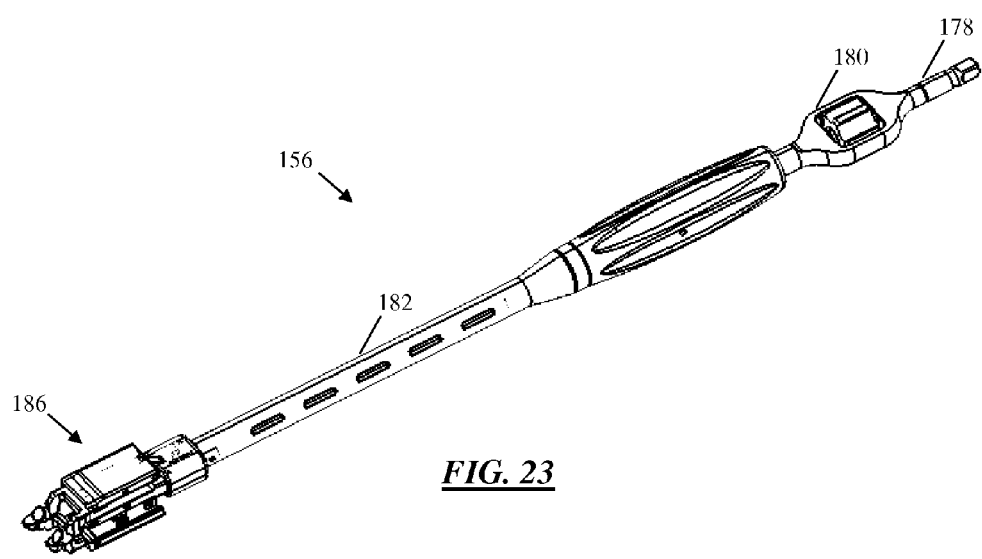
FIG. 23 is an insertion instrument according to a third embodiment.
Figure 24:
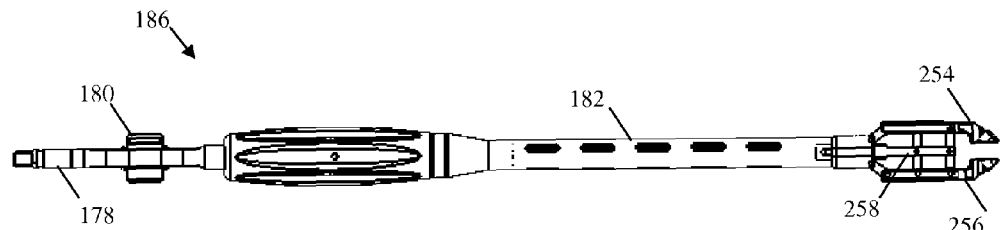
FIG. 24 is a side view of the insertion instrument of FIG. 23.
Figure 25:
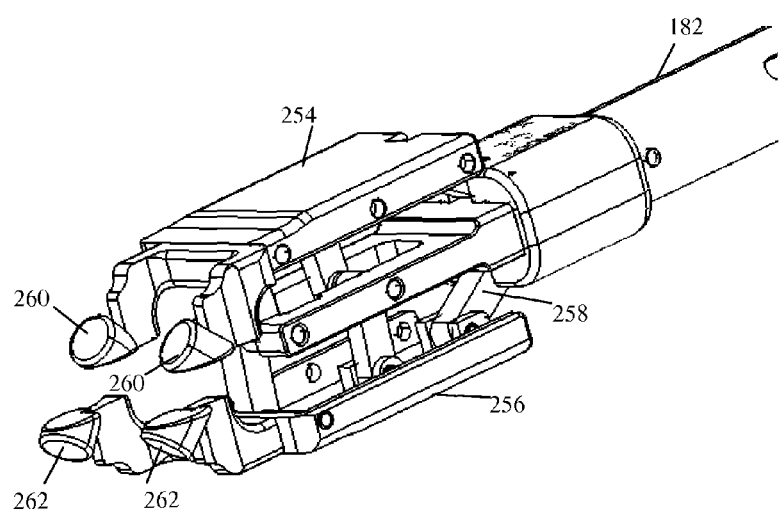
FIG. 25 is a perspective view of the insertion instrument of FIG. 23 in an open position.
Figure 26:
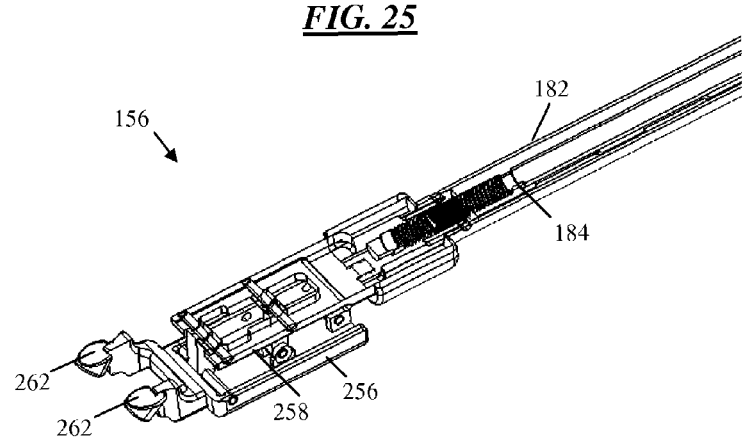
FIG. 26 is a partial cross-sectional view of the insertion instrument of FIG. 23.
Figure 27:
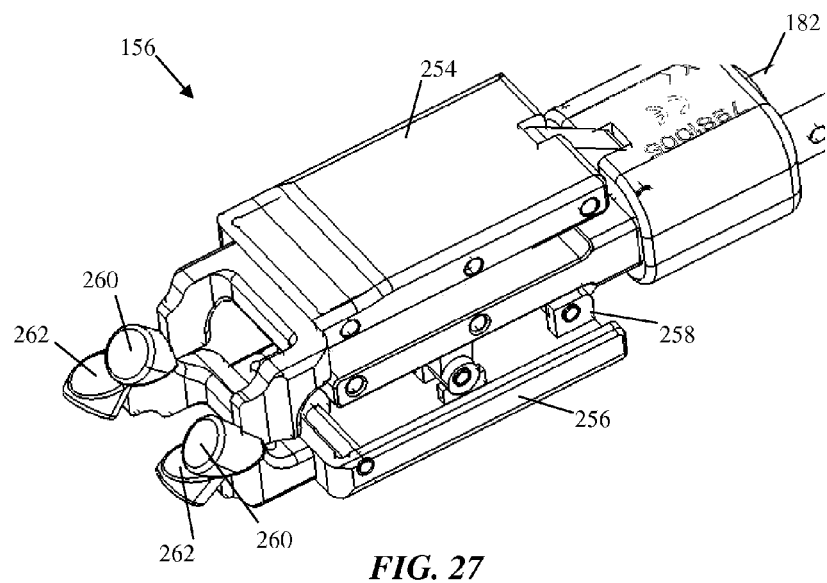
FIG. 27 is a perspective view of the insertion instrument of FIG. 23 in a closed position.
Figure 28:
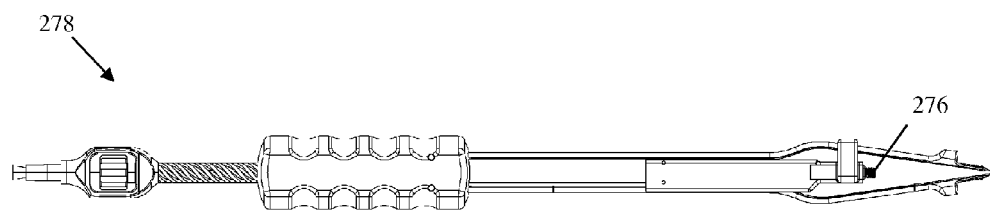
FIG. 28 is a side view of an insertion instrument according to a fourth embodiment.

As best viewed in FIG. 19, the inserter base 228 extends generally obliquely from the elongate tubular member 182 includes a central aperture 232, a lateral notch 234, an guide slot 236 and a fixed gripping arm 238. The central aperture 232 of the inserter base 228 is sized and dimensioned to be slidably received over the inserter shaft 184 at an offset (preferably 60 degrees offset).

The inserter shaft 184 contains a short pin channel 242 adjacent to a recess 240 at its distal end (FIG. 19). The recess 240 is sized and dimensioned to snugly receive the movable gripping arm 230 such that when the short pin channel 242 of the inserter shaft 184 is aligned with the short pin channel 246 of the movable gripping arm 230, a short pin 250 may be slidably received therethrough, providing a fixed point for the moveable gripping arm 230 to move in relation to the inserter shaft 184.

The two gripping arms 238, 240 each contain a terminal gripping hook 248. Moveable gripping arm 230 is seated within the inserter base 228 via the lateral notch 234. The moveable gripping arm 230 contains a long pin channel 246 such that when the long pin channel 246 is aligned with the guide slot 236, a long pin 252 may be slidably received therethrough, providing a fixed point for the moveable gripping arm 230 to move in relation to the inserter body 228.

The initial position of the inserter shaft 184 is fully advanced in a distal direction such that the moveable gripping arm 230 is in the open position (at a maximum offset distance relative to the fixed gripping arm 238). In this open position, the long pin 252 linking the inserter body 228 to the moveable gripping arm 230 is in a first, proximal position. The gripping arms 238, 240 may then be placed adjacent to the engagement grooves 132 of the spinal fusion implant 110. The rotation of the thumbwheel 190 in the clockwise direction causes the inserter shaft 184 to retreat within the elongate tube member 182 which will result in pulling the short pin 250 linkage between the inserter shaft 184 and the moveable gripping arm 230 proximally closer within the elongate tube member 812. The moveable gripping arm 230 is guided medially via the guide slot 236 on the inserter base 228 towards a second, distal position. When the inserter shaft 184 is fully retracted within the elongate tubular member 182, the terminal gripping hooks 248 are releaseably engaged to the engagement groove 132 of the spinal fusion implant 110 such that the insertion instrument 154 is stabilized relative to the spinal fusion implant 110. Once the implant 110 has been successfully inserted into the disc space, the thumbwheel direction is reversed, thereby de-coupling the insertion instrument 154 from the implant 110.

FIGS. 23-27 detail an insertion instrument 156 according to a third embodiment of the present invention, preferably adapted for insertion from an antero-medial approach. The distal insertion head 186 includes a top plate 254 and a bottom plate 256 cooperatively linked via a scissor jack 258. Extending distally from the top plate 254 are two upper engagement plugs 260 sized and dimensioned for insertion within the lower screw holes 124 on the spinal fusion implant 110. Extending distally from the bottom plate 256 are two lower engagement plugs 262 sized and dimensioned for insertion within the upper screw holes 122 on the spinal fusion implant 110.

The initial position of the position of the inserter shaft 184 is fully extended such that the inserter shaft 184 has placed the scissor jack 258 in a closed position with the top 254 and bottom 256 plates at their closest distance with respect to one another. The attachment plugs 260, 262 may then be inserted within their respective screw holes 122, 124. The clockwise rotation of the thumbwheel 190 will cause the inserter shaft 184 to retreat within the elongate tubular element 182. As this occurs, the scissor-jack 258 is actuated to simultaneously raise the top plate 254 and lower the bottom plate 262 such that they are reversibly secured within their respective screw hole 122, 124. Specifically, the upper attachment plugs 260 coupled to the lower screw holes 124 on the implant 110 move upwards and the lower engagement plugs 262 coupled to the upper screw 222 holes on the implant 210 lower such that the engagement plugs 260 attached to the top plate 254 move away from the engagement plugs 260 that are attached to the bottom plate 256 thereby pinching the implant 110 for stable insertion. Once the implant 110 has been successfully inserted into the disc space, the thumbwheel 190 direction can be reversed, thereby de-coupling the inserter instrument 156 from the implant 110.

According to a fourth embodiment, the distal inserter head 186 may be provided as an adaptor attachment 158 for other implant installation devices (as shown and described in FIGS. 28-31). For example, the insertion instrument may be partially comprised of the implant installation device 276 shown and described in commonly-owned and co-pending U.S. patent application Ser. No. 12/378,685 filed Feb. 17, 2009. (Attachment A) The adaptor attachment 158 is comprised of an anterior side 264, a posterior side 266, and a top side 268. The posterior aspect 266 of the insertion adaptor 158 is threadably connected via the threaded aperture 270 to the threaded member 276 of the insertion instrument 278. The gripping arms 272 on the anterior side 264 of the adaptor attachment 258 may then be placed adjacent to the engagement grooves 132 of the spinal fusion implant 110 and may be frictionally fit within the engagement members 132. Once the implant 110 has been successfully inserted into the disc space, light force may be used to de-couple the inserter adaptor 158 and insertion instrument 276 from the implant 110.

Figure 32:
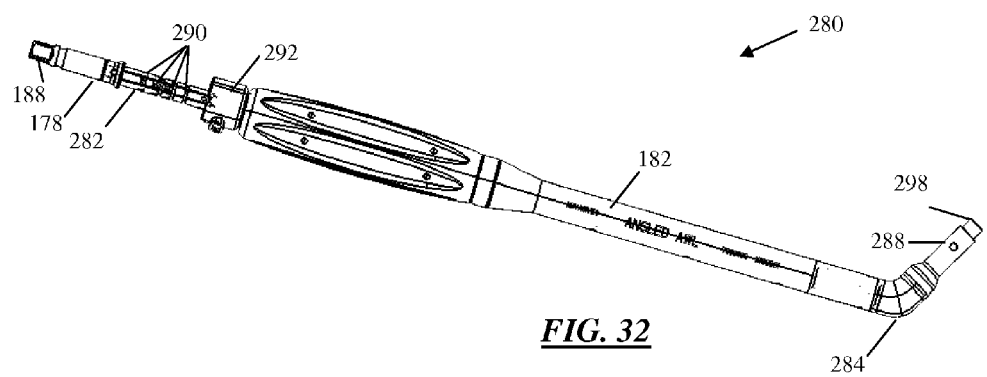
FIG. 32 is a retractable angled awl according to a preferred embodiment.
Figure 33:
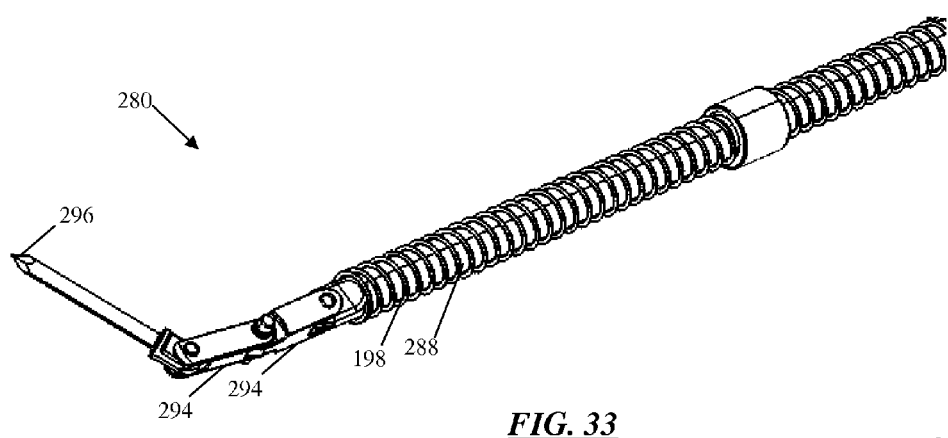
FIG. 33 is a perspective view of the retractable angled awl of FIG. 32 with the cover removed.
Figure 34:
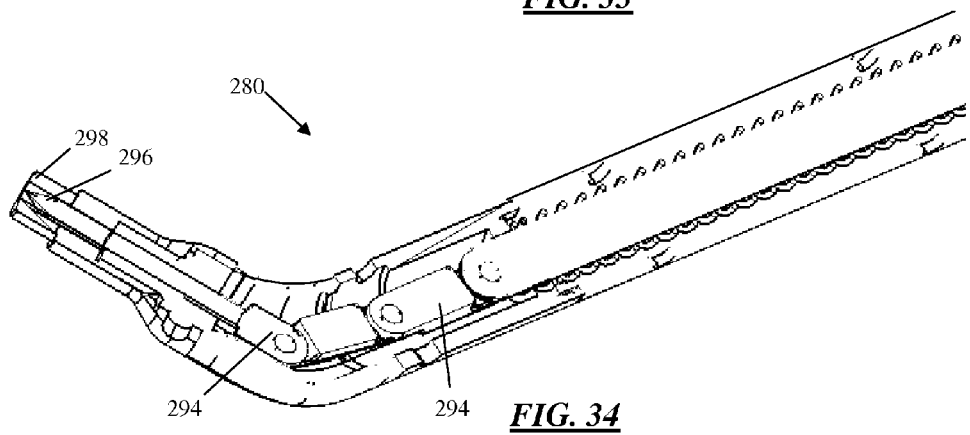
FIG. 34 is a cross-sectional view of the retractable angled awl of FIG. 32.
Figure 35:
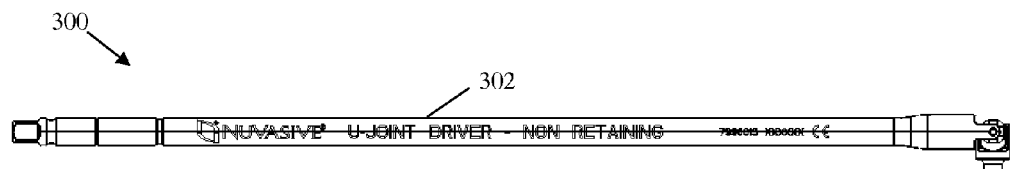
FIG. 35 is an angled driver according to a first embodiment.
Figure 36:
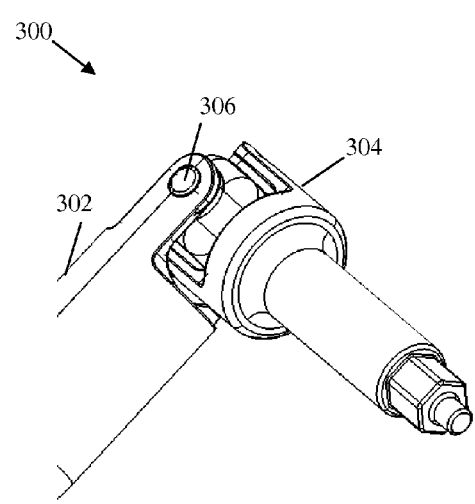
FIG. 36 is a perspective view of the angled driver of FIG. 35
Figure 37:
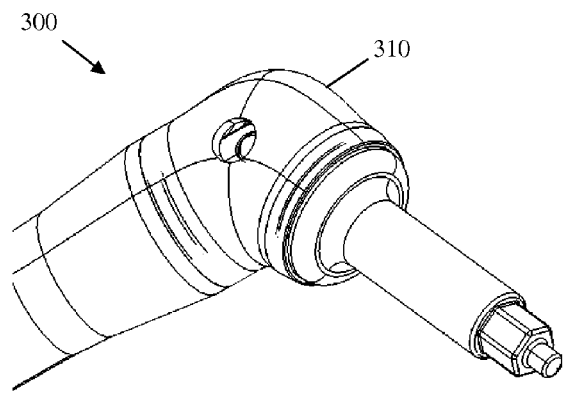
FIG. 37 is a perspective view of the angled driver of FIG. 35 with a cover attached, according to a second embodiment.
Figure 38:
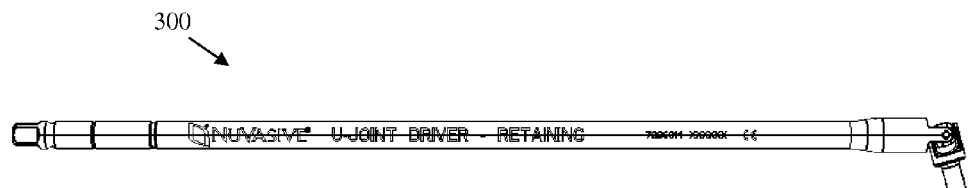
FIG. 38 is an angled driver according to a third embodiment.
Figure 39:
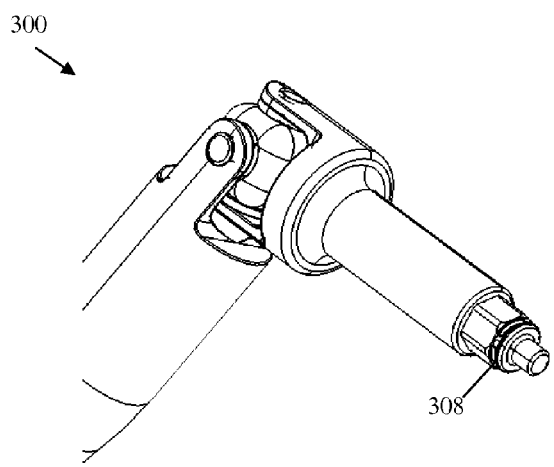
FIG. 39 is a perspective view of the angled driver of FIG. 38.
Figure 40:
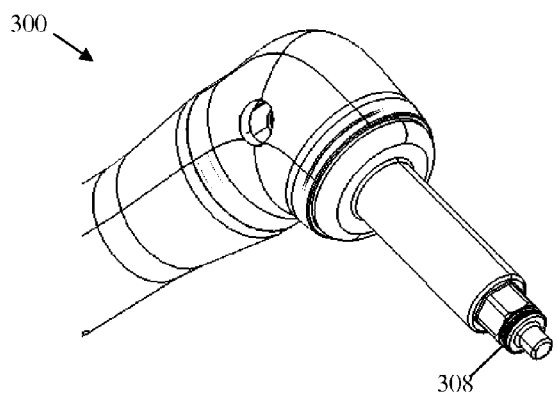
FIG. 40 is a perspective view of the angled driver of FIG. 38 with a cover attached, according to a fourth embodiment.

The present invention further provides a plurality of awls for forming one or more pilot holes in the superior and inferior vertebral bodies to receive bone screws 126. According to a broad aspect of one embodiment, a retractable, angled awl instrument 280 is comprised of a handle 178, an elongate shaft 182, a depth gauge region 282, a transition region 284, and a driver region 288. (FIGS. 32-34).

The handle 178 is generally disposed at the proximal end of the instrument 280. The handle 178 may be further equipped with a universal connector 188 to allow the attachment of accessories for ease of handling of the instrument 280 (e.g. a straight handle, or a T-handle, not shown). The proximal end of the advancement shaft 288 is outfitted with depth markings 290 and a depth selector 292. Once the appropriate depth has been selected, the awl tip 296 is limited to how far it will extend past the cover 298 into the bone. The elongate tubular element 182 is generally cylindrical and of a length sufficient to allow the device to span from the surgical target site to a location sufficiently outside the patient's body so the handle 178 can be easily accessed by a clinician or a complimentary controlling device. The elongate tubular element 182 is dimensioned to receive a spring 196 and the proximal end of the advancement shaft 288 into the inner bore of the elongate tubular element 182. The driver region 286 is composed of an awl tip 296 and a distal cover 298. Transition region 284 contains two linkages 294 for hingedly linking the advancement shaft 288 to the awl tip 296.

In use, the desired depth of tapping is selected on the proximal portion of the instrument 280 by moving the depth selector 292 over the depth marker 290 representing the desired depth. Next, the distal end of the instrument 280 is placed within the screw hole 122, 124. The diameter of the cover 298 bottoms out on the ledge 136 of the screw hole 122, 124 thereby acting as a guide. After the cover 298 bottoms out, the linkages 294 within the transition region 284 drives the awl tip 296 forward. Thus, the awl tip 296 may be used to form pilot holes in line with the axis of the screw hole 122, 124.

FIGS. 35-45 further illustrate a plurality of drivers 300 for use with the present invention thereby providing the user with a host of options for securing the bone screws 126. According to a broad aspect, the drivers may be comprised of an elongate shaft portion 302 coupled to a distal driving portion 304.

According to one embodiment, the drivers may include an elongate shaft portion 302 hingedly coupled to a distal driving portion 304 via a universal joint 306 that engages the screw 126 at a variety of angles (for example, the drivers shown in FIGS. 35-40). According to a second embodiment, the driver 300 may be further provided with a self-retaining hex 308 such that the screw head 144 may be friction fit on the driver 300 during screw delivery (for example, the drivers 300 shown in FIGS. 38-40). According to a third embodiment, the driver 300 may be provided with a sleeve 310 to prevent wrapping of tissue during use (for example, the drivers 300 shown in FIGS. 37 and 40). Use of the sleeve 310 also allows for the driver 300 to engage the screw 126 at a fixed angle of preferably 60 degrees and further allows for more torque to be applied, should patient anatomy or surgeon preference so require.

Figure 41:
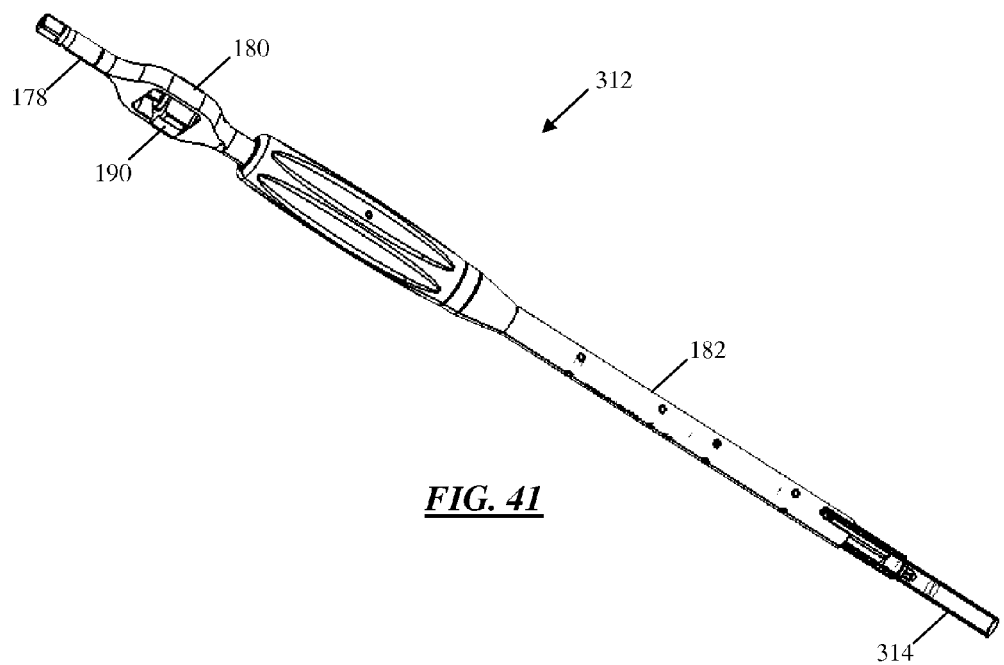
FIG. 41 is a perspective view of a guided straight driver according to a preferred embodiment.
Figure 42:
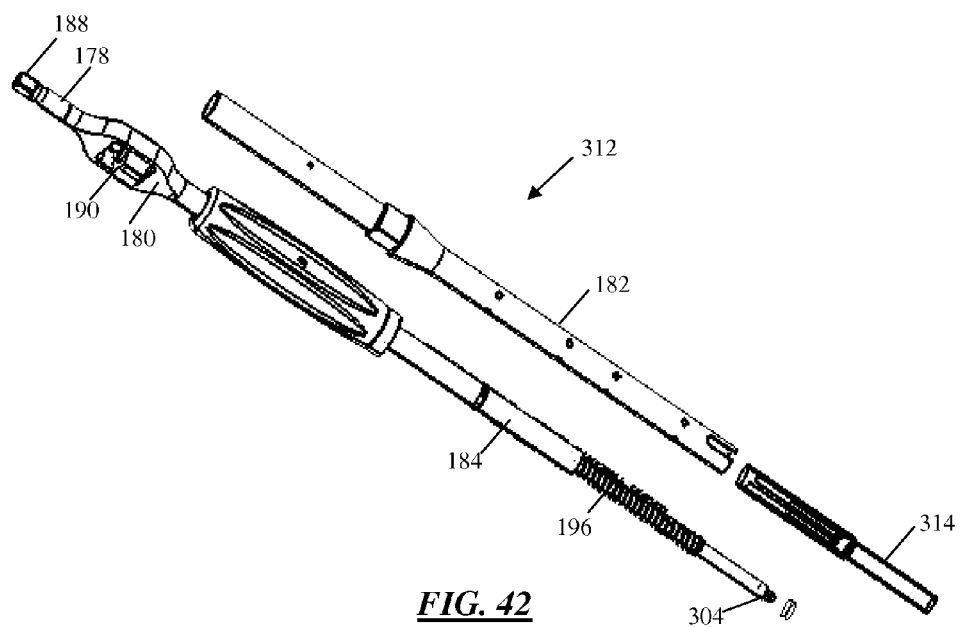
FIG. 42 is an exploded perspective view of the guided straight driver of FIG. 41.

As shown in FIGS. 41-42, a guided straight driver 312 may also be provided. According to a broad aspect of the present invention, the guided straight driver includes a handle 178, a thumbwheel housing 180, an elongate tubular element 182, an inserter shaft 184, a distal driving portion 304, and a distal sheath 314.

The handle 178 is generally disposed at the proximal end of the guided straight driver 312. The handle 178 may be further equipped with a universal connector 188 to allow the attachment of accessories for ease of handling of the insertion instrument 312 (e.g. a straight handle, or a T-handle, not shown). The handle 178 is fixed to the thumbwheel housing 180 allowing easy handling by the user. By way of example, the thumbwheel housing 180 holds a thumbwheel 190, a set screw 192, and at least one spacer 194. Because the handle 178 is fixed, the user has easy access to the thumbwheel 190 and can stably turn the thumbwheel 190 relative to the thumbwheel housing 180. Additionally, the relative orientation of the thumbwheel housing 180 to the handle 178 orients the user with respect to the distal insertion head 186. The inserter shaft 184 is attached to the thumbwheel 190 and is freely rotatable with low friction due to the spacer 194. The user may then employ the thumbwheel 190 to rotate the inserter shaft 184 thereby advancing it towards distal end of the sheath 314.

The elongate tubular element 182 is generally cylindrical and of a length sufficient to allow the device to span from the surgical target site to a location sufficiently outside the patient's body so the handle 178 and thumbwheel housing 180 can be easily accessed by a clinician or a complimentary controlling device. The elongate tubular element 182 is dimensioned to receive a spring 196 and the proximal end of the inserter shaft 184 into the inner bore of the elongate tubular element 182.

The distal end of the guided straight driver 312 is placed within the screwhole 122, 124, the diameter of the sheath 314 bottoms out on the ledge 136 of the screw hole 122, 124 thereby acting as a guide. The initial position of the inserter shaft 184 is fully retracted such that the screw 126 is at a distance proximal to the distal end of the sheath 298. The rotation of the thumbwheel 190 in the clockwise direction causes the inserter shaft 84 to advance within the sheath 314 and drives the screw 126 into the bone.

Figure 43:
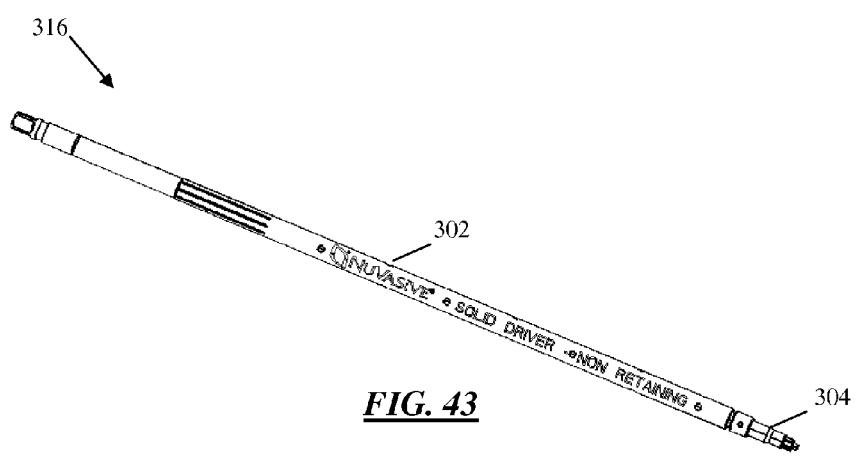
FIG. 43 is a straight driver according to a first embodiment.
Figure 44:
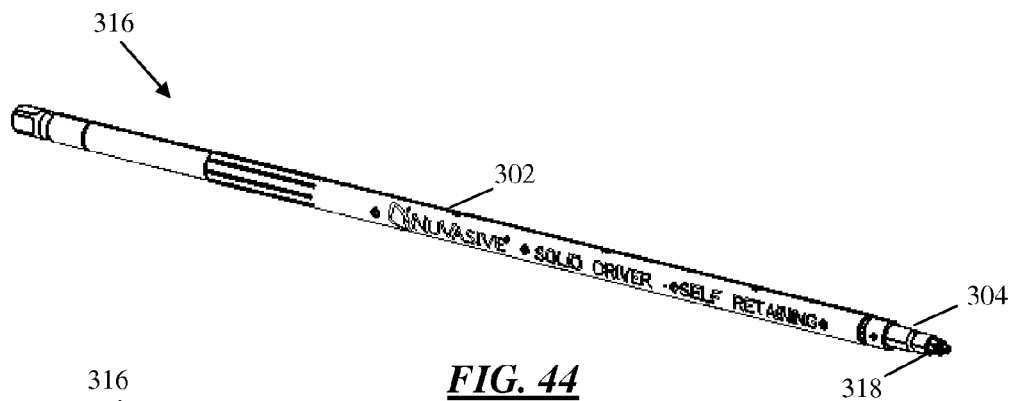
FIG. 44 is a straight driver according to a second embodiment.
Figure 45:
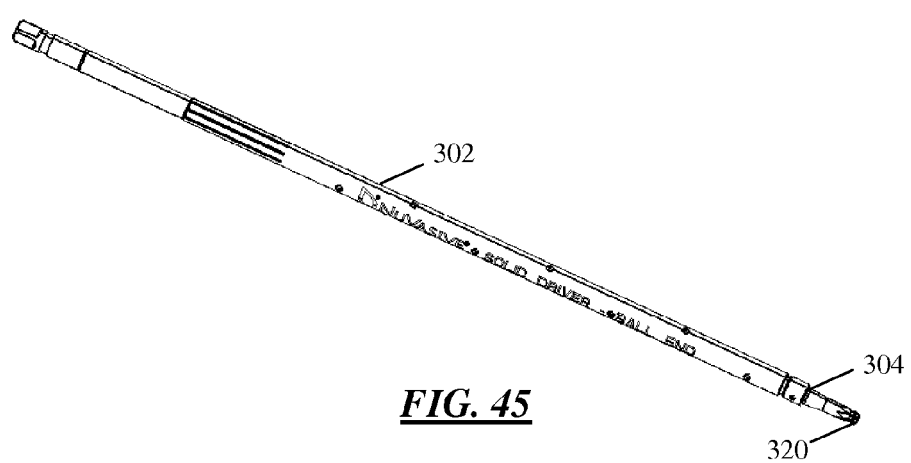
FIG. 45 is a straight driver according to a third embodiment.

As shown in FIGS. 43-45, a straight driver 316 may be provided. Further, the driving portion of the straight driver may be outfitted with a self-retaining hex 318 (FIG. 44) or with a ball end 320 to engage the screw 126 at a variety of angles up to 10 degrees (FIG. 45).

Figure 46:
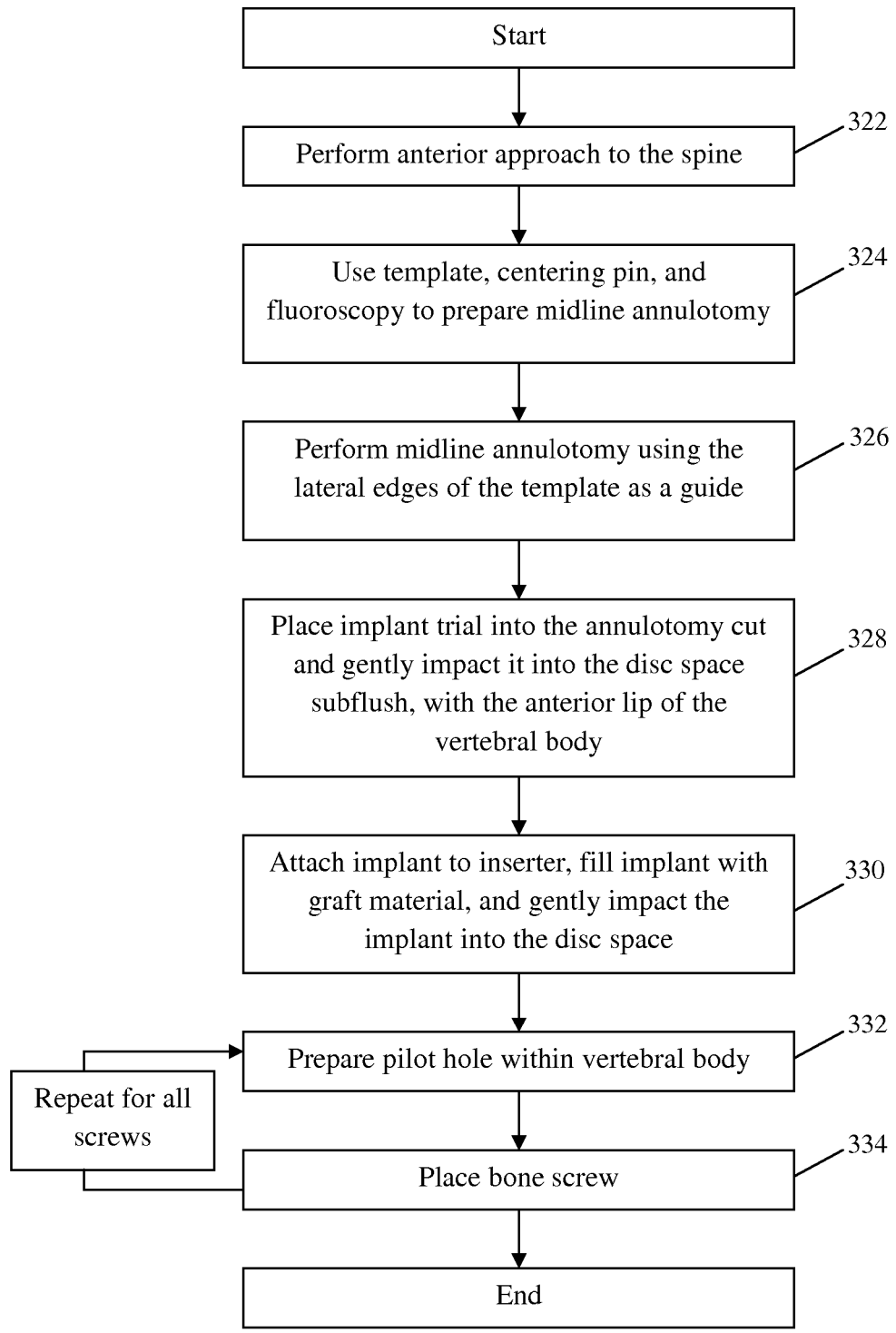
FIG. 46 is a flow chart depicting the steps of implanting the spinal implant of FIG. 1.

As highlighted in the flowchart in FIG. 46, a standard anterior approach to the spine is performed per surgeon preference at step 322. At step 324, an annulotomy template is placed onto the disc space and a centering pin is placed, penetrating the annulus at the midline. The centering pin may have a length of between 10 and 25 mm, preferably 20 mm. Anterior-posterior fluoroscopy may be used to verify midline placement of the centering pin. Additionally, lateral fluoroscopy may be used to check depth. At step 326, a surgical knife is used to cut the annulus, using the lateral edges of the annulotomy template as a guide. Additionally, if the spinal fusion implant is to be further used as a partial vertebral body replacement, the necessary resections may also be made to the vertebral body or bodies. At step 328, a desired trial may be implanted into the annulotomy cut and gently impacted into the disc space such that it is subflush, preferably approximately 2 mm from the anterior lip of the vertebral body. At step 330, the implant corresponding to the appropriate trial side should be selected and attached to the proper size implant inserter (as described above), and filled with an appropriate graft material. The implant is gently impacted into the disc space. Lateral fluoroscopy may be used to confirm proper implant placement. At step 332, the pilot hole is prepared. By way of example only, retractable awl 280 may be used. At step 334, the screw is placed. Steps 332 and 334 may be repeated for each additional screw.

What is claimed is:

1. A spinal fusion implant, comprising:
a body configured for implantation between a superior and an inferior vertebrae, having a top surface and a bottom surface, an anterior height and a posterior height, and a fusion aperture defined by an anterior wall, a posterior wall, and first and second lateral walls;
a plurality of fastener apertures extending through the anterior wall at oblique angles relative to a horizontal axis, each of said fastener apertures dimensioned to receive a bone fastener for insertion into one of the superior or inferior vertebrae, said bone fastener having a head, a shank and a collar disposed between said head and said shank;
wherein said plurality of fastener apertures have an anterior diameter and a posterior diameter, wherein said anterior diameter is greater than said posterior diameter; and
wherein said plurality of fastener apertures comprise an annular groove dimensioned to retain the head of the bone fastener therein,
and wherein said plurality of fastener apertures includes a visualization marker on an exterior-facing surface of each of said plurality of fastener apertures, said visualization marker being partially obscured under direct visualization by said bone faster during insertion of said bone fastener and said entire visualization marker being wholly visible by direct visualization when said bone fastener is fully inserted into said spinal fusion implant.

2. The spinal fusion implant of claim 1, wherein the body is constructed of radiolucent, non-bone material.

3. The spinal fusion implant of claim 1, wherein the anterior height of the body is greater than the posterior height, such that the top surface of the body is oblique to the horizontal axis.

4. The spinal fusion implant of claim 3, wherein the top surface creates a posterior-to-anterior angle relative to the horizontal axis, said posterior-to-anterior angle being between 5° and 15°.

5. The spinal fusion implant of claim 1, wherein the collar of the fastener is at least partially threaded.

6. The spinal fusion implant of claim 1, wherein the fastener apertures further comprise a ledge proximal to the annular groove, wherein the ledge has a diameter that is smaller than the head of the bone fastener, such that the ledge is temporarily deformed while the head of the bone fastener is passing said ledge during insertion.

7. The spinal fusion implant of claim 1, wherein the oblique angles relative to the horizontal axis are between 35° and 55°.

8. The spinal fusion implant of claim 7, wherein the oblique angles relative to the horizontal axis are 45°.

9. The spinal fusion implant of claim 1, wherein said plurality of fastener apertures extend through the anterior wall at angles oblique to a longitudinal axis.

10. The spinal fusion implant of claim 9, wherein the oblique angles relative to the longitudinal axis are convergent.

11. The spinal fusion implant of claim 9, wherein the oblique angles relative to the longitudinal axis are between 5° and 15°.

12. The spinal fusion implant of claim 11, wherein the oblique angles relative to the longitudinal axis are 12°.

13. The spinal fusion implant of claim 1, wherein the plurality of fastener apertures is equal to four.

14. The spinal fusion implant of claim 13, wherein at least two of the fastener apertures are dimensioned to receive the bone fastener for insertion into the inferior vertebrae.

15. The spinal fusion implant of claim 13, wherein at least two of the fastener apertures are dimensioned to receive the bone fastener for insertion into the superior vertebrae.

16. The spinal fusion implant of claim 1, wherein at least one of the top surface and bottom surface includes anti-migration features.

17. The spinal fusion implant of claim 1, wherein the body includes at least one radiopaque marker.

18. The spinal fusion implant of claim 1, wherein the body further comprises an engagement groove in the first and second lateral sides dimensioned to receive a gripping element of an inserter instrument.

* * * * *